United States Patent
Michihata et al.

(10) Patent No.: US 11,962,747 B2
(45) Date of Patent: Apr. 16, 2024

(54) MEDICAL IMAGE PROCESSING DEVICE AND MEDICAL OBSERVATION SYSTEM

(71) Applicant: Sony Olympus Medical Solutions Inc., Tokyo (JP)

(72) Inventors: Taihei Michihata, Tokyo (JP); Aki Mizukami, Tokyo (JP); Kiminori Sugisaki, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 376 days.

(21) Appl. No.: 17/137,380

(22) Filed: Dec. 30, 2020

(65) Prior Publication Data
US 2021/0295502 A1   Sep. 23, 2021

(30) Foreign Application Priority Data
Mar. 18, 2020   (JP) .................................. 2020-048448

(51) Int. Cl.
*H04N 13/257* (2018.01)
*A61B 1/00* (2006.01)
(Continued)

(52) U.S. Cl.
CPC ....... *H04N 13/257* (2018.05); *A61B 1/00009* (2013.01); *A61B 1/00194* (2022.02);
(Continued)

(58) Field of Classification Search
CPC ........................ A61B 1/00163; H04N 13/344; G06T 7/0012; G06T 2207/10064
See application file for complete search history.

(56) References Cited

U.S. PATENT DOCUMENTS 5,822,446 A * 10/1998 Kato .................... G16H 30/20
                                                    382/128
7,258,442 B2 * 8/2007 Noda ..................... A61B 3/14
                                                    351/205
(Continued)

FOREIGN PATENT DOCUMENTS

JP         2018079249 A       5/2018
WO    WO-2016154589 A1 *   9/2016   ........... A61B 1/0005

*Primary Examiner* — John Villecco
*Assistant Examiner* — Courtney Joan Nelson
(74) *Attorney, Agent, or Firm* — XSENSUS LLP

(57) ABSTRACT

A medical image processing device includes: a first captured image acquisition unit configured to acquire a first left-eye image and a first right-eye image; a second captured image acquisition unit configured to acquire a second left-eye image and a second right-eye image; a superimposed image generation unit configured to superimpose corresponding pixels of the first left-eye image and the second left-eye image on each other to generate a left-eye fluorescence superimposed image and superimpose corresponding pixels of the first right-eye image and the second right-eye image on each other to generate a right-eye fluorescence superimposed image; and a display controller configured to generate a display image from the first left-eye and right-eye images, the second left-eye and right-eye images, the left-eye and the right-eye fluorescence superimposed images, wherein the display image includes a stereoscopically observable three-dimensional fluorescence superimposed image generated from the left-eye and the right-eye fluorescence superimposed images.

20 Claims, 8 Drawing Sheets

(51) Int. Cl.
*G06T 7/00* (2017.01)
*H04N 13/344* (2018.01)

(52) U.S. Cl.
CPC ......... *G06T 7/0012* (2013.01); *H04N 13/344* (2018.05); *G06T 2207/10064* (2013.01); *G06T 2207/10068* (2013.01)

(56) References Cited

U.S. PATENT DOCUMENTS

2009/0270678 A1* 10/2009 Scott ............... A61B 1/000096
  600/109
2014/0002468 A1* 1/2014 Sung .................... G09G 5/399
  345/536

* cited by examiner

MEDICAL IMAGE PROCESSING DEVICE AND MEDICAL OBSERVATION SYSTEM

CROSS-REFERENCE TO RELATED APPLICATION

This application claims priority from Japanese Application No. 2020-048448, filed on Mar. 18, 2020, the contents of which are incorporated by reference herein in its entirety.

BACKGROUND

The present disclosure relates to a medical image processing device and a medical observation system.

In the related art, there is known a medical observation system that administers a fluorescent substance such as indocyanine green into a living body and irradiates an observation target with excitation light that excites the fluorescent substance to fluorescently observe a lesion in which the fluorescent substance is accumulated (see, for example, JP 2015-29841 A).

In the medical observation system described in JP 2015-29841 A, the following first and second captured images are acquired and corresponding pixels of the first and second captured images are superimposed on each other to generate a fluorescence superimposed image.

The first captured image is an image obtained by irradiating an observation target with normal light, which is white light, and capturing the normal light reflected by the observation target with an image sensor.

The second captured image is an image obtained by irradiating an observation target with excitation light that excites a fluorescent substance such as indocyanine green and capturing the fluorescence from the observation target excited by the excitation light with a high-sensitivity image sensor.

Further, a doctor excises or sutures a lesion while confirming the fluorescence superimposed image.

SUMMARY

The fluorescence superimposed image displayed by the medical observation system described in JP 2015-29841 A is a two-dimensional image. On the other hand, a three-dimensional image that may be observed stereoscopically has a sense of depth, and thus, the image makes excising or suturing of the lesion easy.

Therefore, there is a demand for a technique capable of improving convenience by generating a three-dimensional fluorescence superimposed image that may be observed stereoscopically.

According to one aspect of the present disclosure, there is provided a medical image processing device including: a first captured image acquisition unit configured to acquire a first left-eye image and a first right-eye image having parallax each of which is obtained by capturing light from an observation target irradiated with light in a first wavelength band, the observation target emitting fluorescence when irradiated with excitation light in a second wavelength band different from the first wavelength band; a second captured image acquisition unit configured to acquire a second left-eye image and a second right-eye image having parallax each of which is obtained by capturing the fluorescence from the observation target irradiated with the excitation light; a superimposed image generation unit configured to superimpose corresponding pixels of the first left-eye image and the second left-eye image on each other to generate a left-eye fluorescence superimposed image and superimpose corresponding pixels of the first right-eye image and the second right-eye image on each other to generate a right-eye fluorescence superimposed image; and a display controller configured to generate a display image from the first left-eye image, the first right-eye image, the second left-eye image, the second right-eye image, the left-eye fluorescence superimposed image, and the right-eye fluorescence superimposed image, wherein the display image includes a stereoscopically observable three-dimensional fluorescence superimposed image generated from the left-eye fluorescence superimposed image and the right-eye fluorescence superimposed image.

DETAILED DESCRIPTION

Hereinafter, a mode (hereinafter, embodiment) for carrying out the present disclosure will be described with reference to the drawings. Incidentally, the present disclosure is not limited to the embodiment to be described below. Further, the same parts are denoted by the same reference signs when the drawings are described.

Schematic Configuration of Medical Observation System

Figure 1:
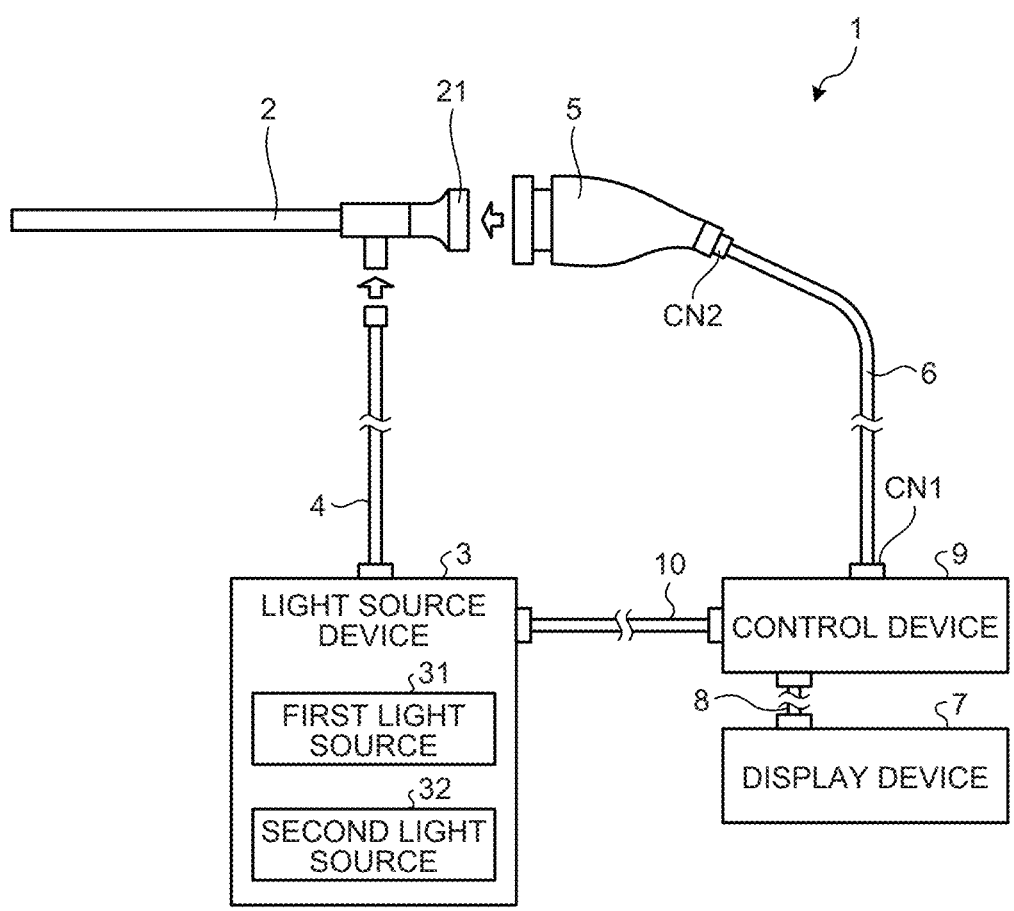
FIG. 1 is a diagram illustrating a configuration of a medical observation system according to an embodiment.

FIG. 1 is a diagram illustrating a configuration of a medical observation system 1 according to the present embodiment.

The medical observation system 1 is a system used in the medical field to capture (observe) the inside of a living body (observation target) as a subject. As illustrated in FIG. 1, the medical observation system 1 includes an insertion section 2, a light source device 3, a light guide 4, a camera head 5, a first transmission cable 6, a display device 7, a second transmission cable 8, a control device 9, and a third transmission cable 10.

The insertion section 2 is configured using a binocular relay type or a monocular pupil-division type scope (rigid endoscope).

Specifically, in the binocular relay type scope, two optical paths are arrayed in parallel in the scope. In addition, an optical system is arranged in each of the two optical paths. Further, the binocular relay type scope takes and emits observation light for left and right eyes having parallax with each other in the two optical systems (see, for example, JP H06-160731 A).

In addition, in the monocular pupil-division type scope, one optical path is provided in the scope. In addition, an optical system is arranged in the one optical path. Further, a pupil division unit that divides luminous flux in the pupil into two areas is provided at a pupil position of the optical system. Further, the monocular pupil-division type scope takes observation light in the optical system, divides the observation light into observation light for left and right eyes having parallax by the pupil division unit, and emits the divided observation light (see, for example, JP H06-59199 A).

One end of the light guide 4 is connected with the light source device 3, and supplies light that irradiates the inside of a living body to the one end of the light guide 4 under the control of the control device 9. As illustrated in FIG. 1, the light source device 3 includes a first light source 31 and a second light source 32.

The first light source 31 outputs (emits) light in a first wavelength band. In the present embodiment, the first light source 31 is configured using an element that emits white light (light in the first wavelength band). As the element that emits light, for example, a light emitting diode (LED) or a laser diode (LD), which is a semiconductor element, may be used.

The second light source 32 outputs (emits) excitation light in a second wavelength band different from the first wavelength band. In the present embodiment, the second light source 32 is configured using an element that emits near-infrared excitation light (excitation light in the second wavelength band). As the element that emits light, for example, an LED or an LD which is a semiconductor element may be used.

The near-infrared excitation light emitted by the second light source 32 is excitation light that excites a fluorescent substance such as indocyanine green. In addition, when being excited with the near-infrared excitation light, the fluorescent substance such as indocyanine green emits fluorescence having a center wavelength on the longer wavelength side with respect to a center wavelength of a wavelength band of the near-infrared excitation light. Incidentally, the wavelength band of the near-infrared excitation light and the wavelength band of the fluorescence may be set so as to partially overlap with each other, or may be set so as not to overlap at all.

Further, the first light source 31 is driven in a normal observation mode under the control of the control device 9 in the light source device 3 according to the present embodiment. That is, the light source device 3 emits normal light (white light) in the normal observation mode. The normal observation mode corresponds to a second observation mode according to the present disclosure. On the other hand, in a fluorescence observation mode of the light source device 3, the first light source 31 is driven in a first period and the second light source 32 is driven in a second period between the first and second periods that are alternately repeated under the control of the control device 9. That is, in the fluorescence observation mode, the light source device 3 emits normal light (white light) in the first period and emits near-infrared excitation light in the second period. The fluorescence observation mode corresponds to a first observation mode according to the present disclosure.

Incidentally, the light source device 3 is configured as a separate body from the control device 9 in the present embodiment, but may adopt a configuration of being provided inside the control device 9 without being limited thereto.

The one end of the light guide 4 is detachably connected with the light source device 3, and the other end thereof is detachably connected to the insertion section 2. Further, the light guide 4 transmits light (normal light or near-infrared excitation light) supplied from the light source device 3 from one end to the other end and supplies the light to the insertion section 2. When the inside of the living body is irradiated with the normal light (white light), the normal light reflected in the living body is collected in the insertion section 2. Incidentally, for convenience of the description, the normal light as observation light for left and right eyes, collected in the insertion section 2 and emitted from the insertion section 2, is described as first left-eye and right-eye subject images hereinafter. In addition, when the inside of a living body is irradiated with near-infrared excitation light, the near-infrared excitation light reflected in the living body and fluorescence emitted from a fluorescent substance, such as indocyanine green, accumulated in a lesion in the living body, as the fluorescent substance is excited, are collected in the insertion section 2. Incidentally, for convenience of the description, the near-infrared excitation light and fluorescence light as observation light for left and right eyes, collected in the insertion section 2 and emitted from the insertion section 2, is described as second left-eye and right-eye subject images hereinafter.

The camera head 5 corresponds to an imaging device according to the present disclosure. The camera head 5 is detachably connected to a proximal end (eyepiece 21 (FIG. 1)) of the insertion section 2. Further, the camera head 5 captures the first left-eye and right-eye subject images (normal light) and the second left-eye and right-eye subject images (near-infrared excitation light and fluorescence) emitted from the insertion section 2 and outputs an image signal obtained by the capturing under the control of the control device 9.

Incidentally, a detailed configuration of the camera head 5 will be described later.

One end of the first transmission cable 6 is detachably connected with the control device 9 via a connector CN1 (FIG. 1), and the other end thereof is detachably connected with the camera head 5 via a connector CN2 (FIG. 1). Further, the first transmission cable 6 transmits the image signal and the like output from the camera head 5 to the control device 9, and transmits each of a control signal output from the control device 9, a synchronization signal, a clock signal, power, and the like, to the camera head 5.

Incidentally, in the transmission of the image signal or the like from the camera head 5 to the control device 9 via the first transmission cable 6, the image signal or the like may be transmitted as an optical signal or may be transmitted as an electrical signal. The same applies to the transmission of the control signal, the synchronization signal, and the clock signal from the control device 9 to the camera head 5 via the first transmission cable 6.

The display device 7 displays an image based on a video signal from the control device 9.

One end of the second transmission cable 8 is detachably connected with the display device 7, and the other end thereof is detachably connected with the control device 9. Further, the second transmission cable 8 transmits the video signal processed by the control device 9 to the display device 7.

The control device 9 corresponds to a medical image processing device according to the present disclosure. The control device 9 is configured using a central processing unit (CPU), a field-programmable gate array (FPGA), or the like, and performs the overall control of operations of the light source device 3, the camera head 5, and the display device 7.

Incidentally, a detailed configuration of the control device 9 will be described later.

One end of the third transmission cable 10 is detachably connected with the light source device 3, and the other end thereof is detachably connected with the control device 9. Further, the third transmission cable 10 transmits the control signal from the control device 9 to the light source device 3.

Configuration of Camera Head

Next, the configuration of the camera head 5 will be described.

Figure 2:
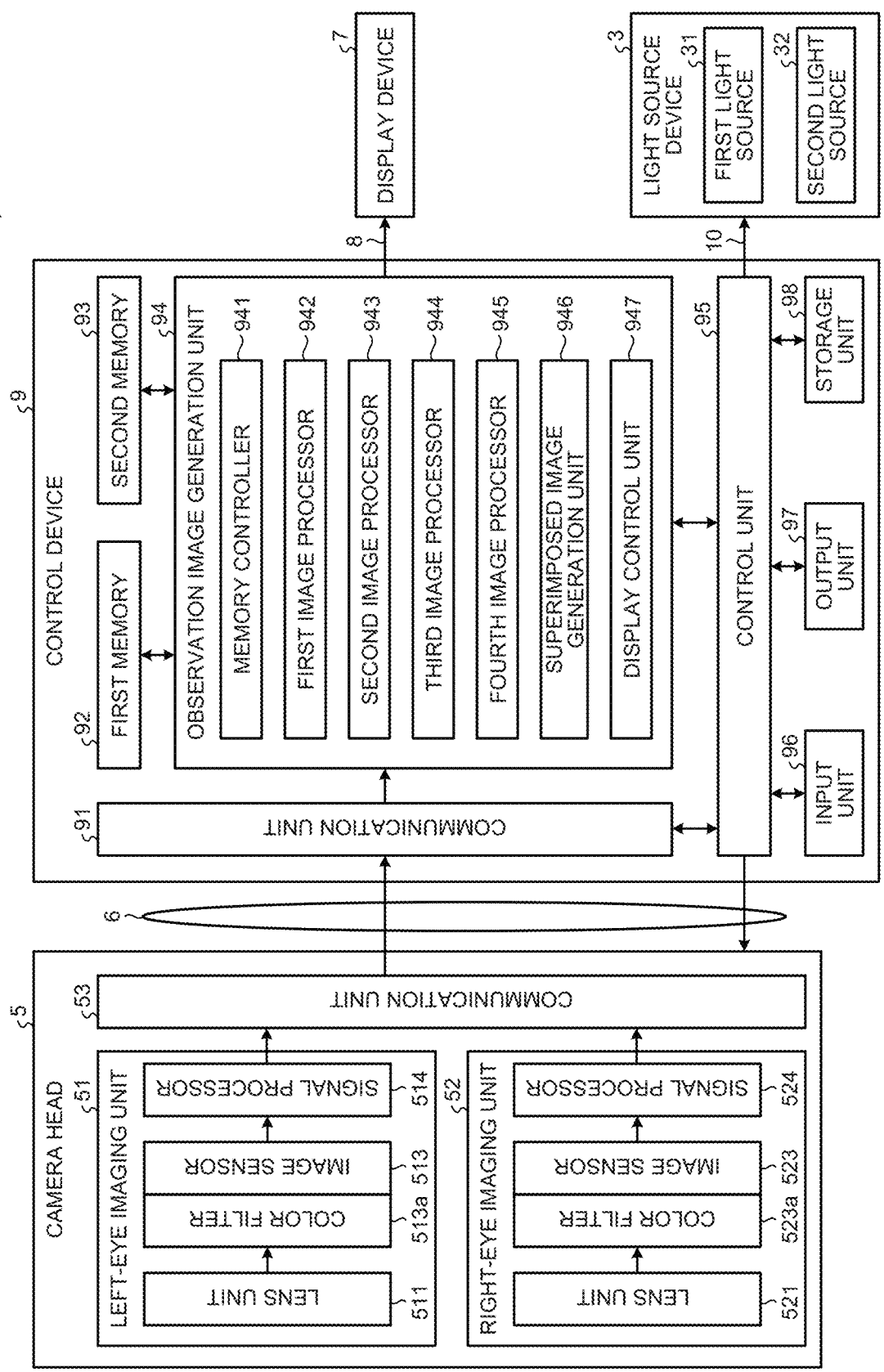
FIG. 2 is a block diagram illustrating configurations of a camera head and a control device.

FIG. 2 is a block diagram illustrating the configurations of the camera head 5 and the control device 9.

Incidentally, FIG. 2 does not illustrate the connectors CN1 and CN2 between the control device 9 and the camera head 5, and the first transmission cable 6, a connector between the control device 9 and the display device 7, and the second transmission cable 8, and a connector between the control device 9 and the light source device 3, and the third transmission cable 10 for convenience of the description.

As illustrated in FIG. 2, the camera head 5 includes left-eye and right-eye imaging units 51 and 52 and a communication unit 53.

The left-eye imaging unit 51 captures the first left-eye subject image (normal light) and the second left-eye subject image (near-infrared excitation light and fluorescence) emitted from the insertion section 2 under the control of the control device 9. As illustrated in FIG. 2, the left-eye imaging unit 51 includes a lens unit 511, an image sensor 513, and a signal processor 514.

The lens unit 511 is configured using one or a plurality of lenses, and forms the first left-eye subject image (normal light) and the second left-eye subject image (near-infrared excitation light and fluorescence) emitted from the insertion section 2 on an imaging surface of the image sensor 513.

The image sensor 513 corresponds to a first image sensor according to the present disclosure. The image sensor 513 is configured using a charge coupled device (CCD), a complementary metal oxide semiconductor (CMOS), or the like which optically receives light and converts the received light into an electrical signal (analog signal).

Here, on the imaging surface (light-receiving surface) of the image sensor 513, a color filter 513a (FIG. 2) in which three filter groups grouped according to wavelength bands of transmitted light (R (red), G (green), and B (blue)) are arranged in a predetermined format (for example, a Bayer array) is provided.

Specifically, the color filter 513a has an R filter group that mainly transmits light in the wavelength band of R, a B filter group that mainly transmits light in the wavelength band of B, and a G filter group that mainly transmits light in the wavelength band of G.

Incidentally, the respective R, G, and B filter groups also transmit near-infrared excitation light and fluorescence. Further, the image sensor 513 has sensitivity not only to light in the wavelength bands of R, G, and B, but also to light in wavelength bands of the near-infrared excitation light and fluorescence.

Under the control of the control device 9, the image sensor 513 captures the first left-eye subject image (normal light) at a predetermined frame rate in the normal observation mode. In addition, under the control of the control device 9, the image sensor 513 performs capturing in the fluorescence observation mode for each of the first and second periods, which are alternately repeated, in synchronization with the light emission timing of the light source device 3.

Hereinafter, for convenience of the description, an image, generated by capturing the first left-eye subject image (normal light) with the image sensor 513, is described as a left-eye normal light image (corresponding to a first left-eye image according to the present disclosure). In addition, an image, generated by capturing the second left-eye subject image (near-infrared excitation light and fluorescence) with the image sensor 513, is described as a left-eye fluorescence image (corresponding to a second left-eye image according to the present disclosure). In addition, the left-eye normal light image and the left-eye fluorescence image are collectively described as a left-eye captured image.

The signal processor 514 performs signal processing on the left-eye captured image (analog signal) generated by the image sensor 513.

The right-eye imaging unit 52 captures the first right-eye subject image (normal light) and the second right-eye subject image (near-infrared excitation light and fluorescence) emitted from the insertion section 2 under the control of the control device 9. As illustrated in FIG. 2, the right-eye imaging unit 52 includes a lens unit 521, an image sensor 523 (color filter 523a), and a signal processor 524, which are similar to the lens unit 511, the image sensor 513 (including the color filter 513a), and the signal processor 514 in the left-eye imaging unit 51.

The image sensor 523 corresponds to a second image sensor according to the present disclosure. Under the control of the control device 9, the image sensor 523 captures the first right-eye subject image (normal light) at a predetermined frame rate in the normal observation mode. In addition, under the control of the control device 9, the image sensor 523 performs capturing in the fluorescence observation mode for each of the first and second periods, which are alternately repeated, in synchronization with the light emission timing of the light source device 3.

Hereinafter, for convenience of the description, an image, generated by capturing the first right-eye subject image (normal light) with the image sensor 523, is described as a right-eye normal light image (corresponding to a first right-eye image according to the present disclosure). In addition, an image, generated by capturing the second right-eye subject image (near-infrared excitation light and fluorescence) with the image sensor 523, is described as a right-eye fluorescence image (corresponding to a second right-eye image according to the present disclosure). In addition, the right-eye normal light image and the right-eye fluorescence image are collectively described as a right-eye captured image.

Further, the right-eye imaging unit 52 performs signal processing by the signal processor 524 similarly to the left-eye imaging unit 51.

The communication unit 53 functions as a transmitter that transmits the left-eye captured images in raster units, which are sequentially output from the left-eye imaging unit 51 and the right-eye captured images in raster units, which are sequentially output from the right-eye imaging unit 52, to the control device 9 via the first transmission cable 6.

Configuration of Control Device

Next, the configuration of the control device 9 will be described with reference to FIG. 2.

As illustrated in FIG. 2, the control device 9 includes a communication unit 91, first and second memories 92 and 93, an observation image generation unit 94, a control unit 95, an input unit 96, an output unit 97, and a storage unit 98.

The communication unit 91 functions as a receiver that receives the left-eye and right-eye captured images in raster units which are sequentially output from the camera head 5 (communication unit 53) via the first transmission cable 6. The communication unit 91 corresponds to a first captured image acquisition unit and a second captured image acquisition unit according to the present disclosure.

The first memory 92 temporarily stores the left-eye and right-eye captured images sequentially output from the camera head 5 (communication unit 53).

The second memory 93 temporarily stores the image processed by the observation image generation unit 94.

Under the control of the control unit 95, the observation image generation unit 94 processes the left-eye and right-eye captured images in raster units which are sequentially output from the camera head 5 (communication unit 53) and received by the communication unit 91. As illustrated in FIG. 2, the observation image generation unit 94 includes a memory controller 941, first to fourth image processors 942 to 945, a superimposed image generation unit 946, and a display control unit 947.

The memory controller 941 controls writing of an image to the first memory 92 and reading of an image from the first memory 92 under the control of the control unit 95. Incidentally, details of the function of the memory controller 941 will be described in "Operation of Control Device" which will be described later.

The first to fourth image processors 942 to 945 execute image processing in parallel on each of input images under the control of the control unit 95.

Incidentally, the first to fourth image processors 942 to 945 have the same configuration.

The superimposed image generation unit 946 operates only in the fluorescence observation mode under the control of the control unit 95. Further, the superimposed image generation unit 946 generates left-eye and right-eye fluorescence superimposed images based on the images on which image processing has been executed by the first to fourth image processors 942 to 945. Incidentally, details of the left-eye and right-eye fluorescence superimposed images will be described in "Operation of Control Device" which will be described later.

The display control unit 947 generates a display image from the images on which the image processing has been executed by the first to fourth image processors 942 to 945 and the left-eye and right-eye fluorescence superimposed images generated by the superimposed image generation unit 946. Further, the display control unit 947 outputs a video signal for display of the display image to the display device 7 via the second transmission cable 8.

Incidentally, details of the function of the display control unit 947 will be described in "Operation of Control Device" which will be described later.

The control unit 95 is configured using, for example, a CPU, an FPGA, or the like, and outputs a control signal via the first to third transmission cables 6, 8, and 10 to control the operations of the light source device 3, the camera head 5, and the display device 7 and control the entire operation of the control device 9. Incidentally, details of the function of the control unit 95 will be described in "Operation of Control device" which will be described later.

The input unit 96 is configured using an operation device such as a mouse, a keyboard, and a touch panel, and receives a user operation performed by a user such as a doctor. Further, the input unit 96 outputs an operation signal corresponding to the user operation to the control unit 95.

The output unit 97 is configured using a speaker, a touch panel, or the like, and outputs various types of information.

The storage unit 98 stores a program executed by the control unit 95, information necessary for processing of the control unit 95, and the like.

Operation of Control Device

Next, the operation of the control device 9 described above will be described.

Figure 3:
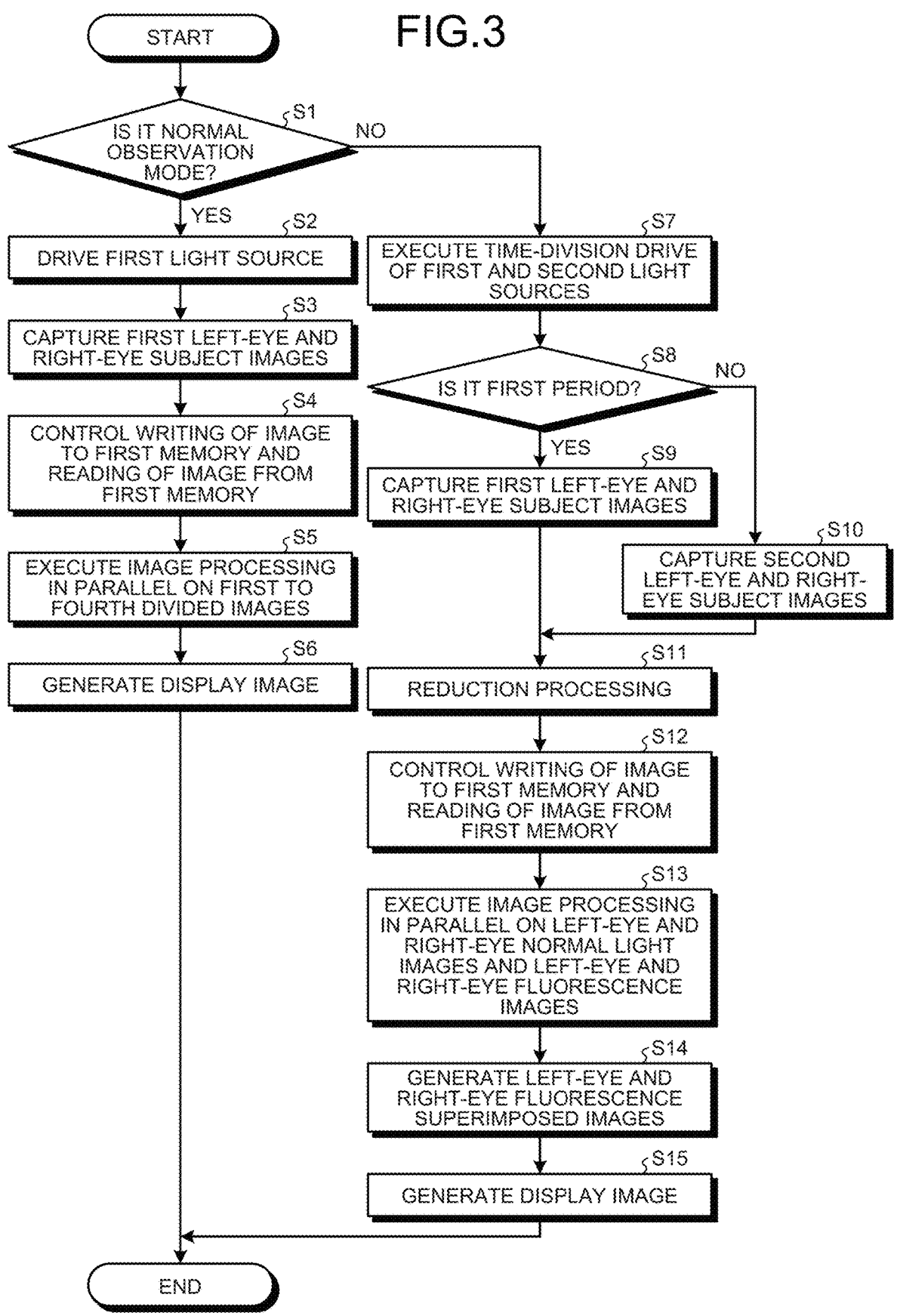
FIG. 3 is a flowchart illustrating an operation of the control device.

FIG. 3 is a flowchart illustrating the operation of the control device 9.

Incidentally, hereinafter, it is assumed that the image sensors 513 and 523 are image sensors that generate left-eye and right-eye captured images having the number of pixels of 4K. In addition, it is assumed that the maximum amount of data that may be processed by the first image processor 942 is the amount of data of an image having the number of pixels of full HD. The same applies to the other second to fourth image processors 943 to 945.

First, the control unit 95 determines whether a current mode of the control device 9 is the normal observation mode (Step S1).

Incidentally, the mode of the control device 9 is switched by the control unit 95. Specifically, the control unit 95 switches the mode of the control device 9 to the normal observation mode or the fluorescence observation mode in response to a user operation on the input unit 96 by a user such as a doctor. That is, the control unit 95 has a function as a mode switching unit according to the present disclosure.

When determining that the current mode is the normal observation mode (Step S1: Yes), the control unit 95 drives the first light source 31 (Step S2). That is, the inside of the living body is irradiated with normal light (white light).

After Step S2, the control unit 95 causes the image sensors 513 and 523 to capture the first left-eye and right-eye subject images (normal light) at a predetermined frame rate (Step S3). Further, the left-eye and right-eye imaging units 51 and 52 sequentially output the left-eye and right-eye normal light images each having the number of pixels of 4K in raster units.

After Step S3, the memory controller 941 controls writing of an image to the first memory 92 and reading of an image from the first memory 92 (Step S4).

Figure 4:
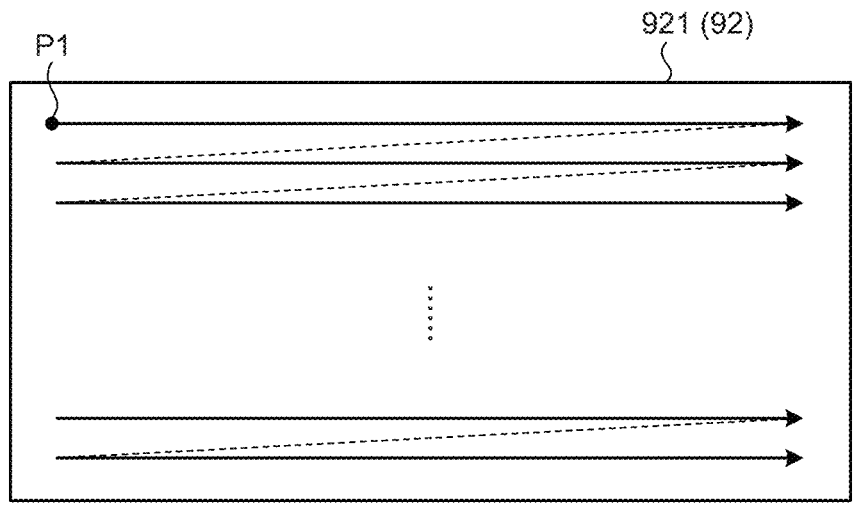
FIG. 4 is a view illustrating an operation of a memory controller in a normal observation mode.
Figure 5:
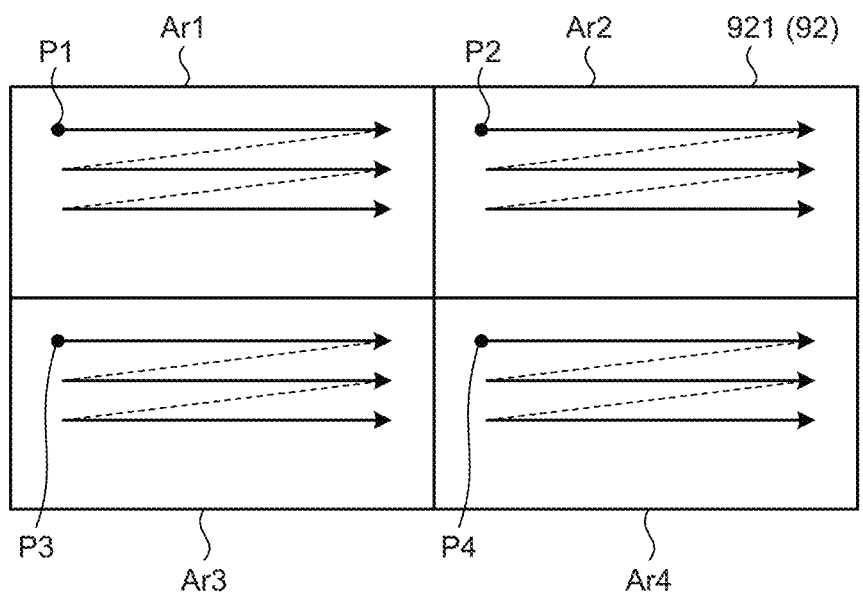
FIG. 5 is a view illustrating the operation of the memory controller in the normal observation mode.

FIGS. 4 and 5 are views illustrating the operation of the memory controller 941 in the normal observation mode. Specifically, FIG. 4 is a view illustrating writing of the left-eye normal light image to the first memory 92. FIG. 5 is a view illustrating reading of the left-eye normal light image from the first memory 92. Incidentally, FIGS. 4 and 5 schematically illustrate a specific bank 921 among a plurality of banks in the first memory 92. The bank 921 corresponds to a fifth memory area according to the present disclosure, and has a memory capacity corresponding to the amount of data of an image having the number of pixels of 4K in the present embodiment. In addition, the entire area in the bank 921 is evenly divided into four areas of first to fourth divided areas Ar1 to Ar4 in a rice crossed square shape in FIG. 5. That is, in the present embodiment, each of the first to fourth divided areas Ar1 to Ar4 has a memory capacity corresponding to the amount of data of an image having the number of pixels of full HD. The first to fourth divided areas Ar1 to Ar4 correspond to divided areas according to the present disclosure.

Specifically, the memory controller 941 sequentially writes the left-eye normal light images in raster units (the number of pixels: 4K), sequentially output from the left-eye imaging unit 51 and received by the communication unit 91, to the bank 921 per line as indicated by arrows and broken lines in FIG. 4. Here, one arrow illustrated in FIG. 4 indicates an image for one line in the left-eye normal light image (the number of pixels: 4K). Incidentally, the right-eye normal light images in raster units, sequentially output from the right-eye imaging unit 52 and received by the communication unit 91, are not used in the processing in Step S4 and the subsequent steps.

In addition, the memory controller 941 reads images written in the first to fourth divided areas Ar1 to Ar4 sequentially from the first to fourth storage positions P1 to P4 per line as indicated by arrows and dashed lines in FIG. 5 substantially at the same time as the timing of writing one frame of the left-eye normal light image (the number of pixels: 4K) to the fourth storage position P4 (FIG. 5).

Here, an image written in the first divided area Ar1 (hereinafter, referred to as a first divided image) is an image in a rectangular area including an upper left corner position of the left-eye normal light image. Further, pixel data stored at the first storage position P1 is pixel data of a pixel at an upper left corner position in the first divided image. In addition, an image written in the second divided area Ar2 (hereinafter referred to as a second divided image) is an image in a rectangular area including an upper right corner position of the left-eye normal light image. Further, pixel data stored at the second storage position P2 is pixel data of a pixel at an upper left corner position in the second divided image. Further, an image written in the third divided area Ar3 (hereinafter referred to as a third divided image) is an image in a rectangular area including a lower left corner position in the left-eye normal light image. Further, pixel data stored at the third storage position P3 is pixel data of a pixel at an upper left corner position in the third divided image. In addition, an image written in the fourth divided area Ar4 (hereinafter referred to as a fourth divided image) is an image in a rectangular area including a lower right corner position of the left-eye normal light image. Further, pixel data stored at the fourth storage position P4 is pixel data of a pixel at an upper left corner position in the fourth divided image.

The first to fourth divided images described above are images obtained by evenly dividing the left-eye normal light image having the number of pixels of 4K into four images, and thus, each of the images has the number of pixels of full HD.

Further, the read first to fourth divided images (the number of pixels: full HD) are sequentially input to the first to fourth image processors 942 to 945 per line. Incidentally, one arrow illustrated in FIG. 5 indicates an image for one line in the first to fourth divided images (the number of pixels: full HD).

After Step S4, the first to fourth image processors 942 to 945 execute image processing in parallel on the input first to fourth divided images (the number of pixels: full HD) (Step S5). After Step S5, the display control unit 947 generates a display image (left-eye normal light image (the number of pixels: 4K)) obtained by combining the first to fourth divided images on which the first image processing has been executed (Step S6). Further, the display control unit 947 outputs a video signal for display of the left-eye normal light image (the number of pixels: 4K) to the display device 7 via the second transmission cable 8. As a result, the display device 7 displays the left-eye normal light image (the number of pixels: 4K) based on the video signal.

Although the left-eye normal light image is used in Steps S4 to S6 described above, the right-eye normal light image may be used without being limited thereto. Incidentally, the drive (capturing) of the image sensor, that captures an image not used in Steps S4 to S6, between the image sensors 513 and 523 may be stopped in Step S3.

When returning to Step S1 and determining that the current mode is the fluorescence observation mode (Step S1: No), the control unit 95 executes time-division drive of the first and second light sources 31 and 32 (Step S7). Specifically, in Step S7, the control unit 95 causes the first light source 31 to emit light in the first period between the first and second periods which are alternately repeated, and causes the second light source 32 to emit light in the second period based on the synchronization signal.

After Step S7, the control unit 95 causes the light emission timings of the first and second light sources 31 and 32 to synchronize with each other based on the synchronization signal, and causes the left-eye and right-eye imaging units 51 and 52 to capture the first left-eye and right-eye subject images and the second left-eye and right-eye subject images in the first and second periods, respectively (Steps S8 to S11). That is, in the first period (Step 38: Yes), in other words, when the inside of the living body is irradiated with normal light (white light), the image sensors 513 and 523 capture the first left-eye and right-eye subject images (normal light) to generate the left-eye and right-eye normal light images (Step S9). On the other hand, in the second period (Step S8: No), in other words, when the living body is irradiated with near-infrared excitation light, the image sensors 513 and 523 capture the second left-eye and right-eye subject images (near-infrared excitation light and fluorescence) to generate the left-eye and right-eye fluorescence images (Step S10). In addition, the signal processors 514 and 524 execute reduction processing (Step S11). With the reduction processing, the left-eye and right-eye normal light images and the left-eye and right-eye fluorescence images each having the number of pixels of 4K are converted into the left-eye and right-eye normal light images and the left-eye and right-eye fluorescence images each having the number of pixels of full HD, respectively.

Further, the left-eye and right-eye imaging units 51 and 52 output the left-eye and right-eye normal light images having the number of pixels of full HD and obtained by capturing in the first period. In addition, the left-eye and right-eye imaging units 51 and 52 output the left-eye and right-eye fluorescence images having the number of pixels of full HD and obtained by capturing in the second period.

After Step S11, the memory controller 941 controls writing of an image to the first memory 92 and reading of an image from the first memory 92 (Step S12).

Figure 6:
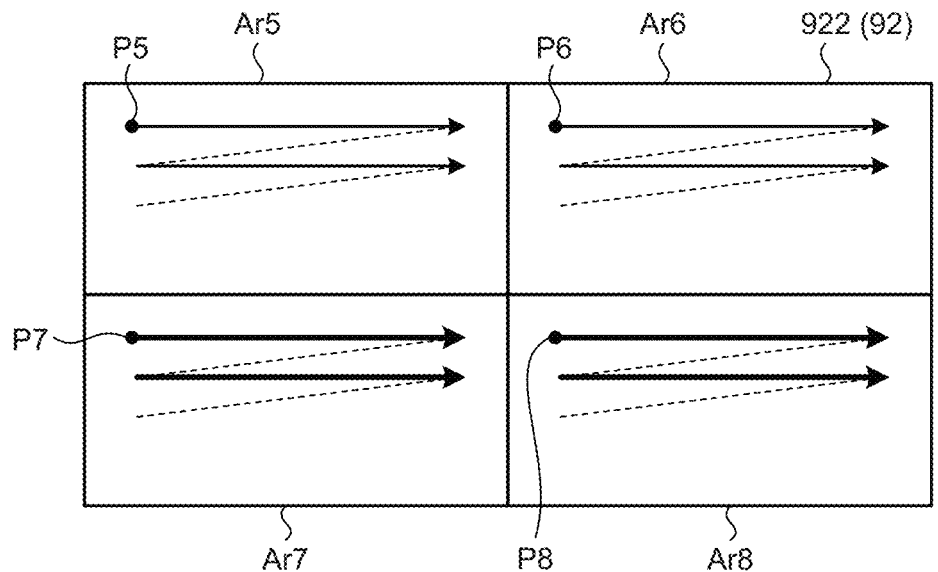
FIG. 6 is a view illustrating an operation of the memory controller in a fluorescence observation mode.
Figure 7:
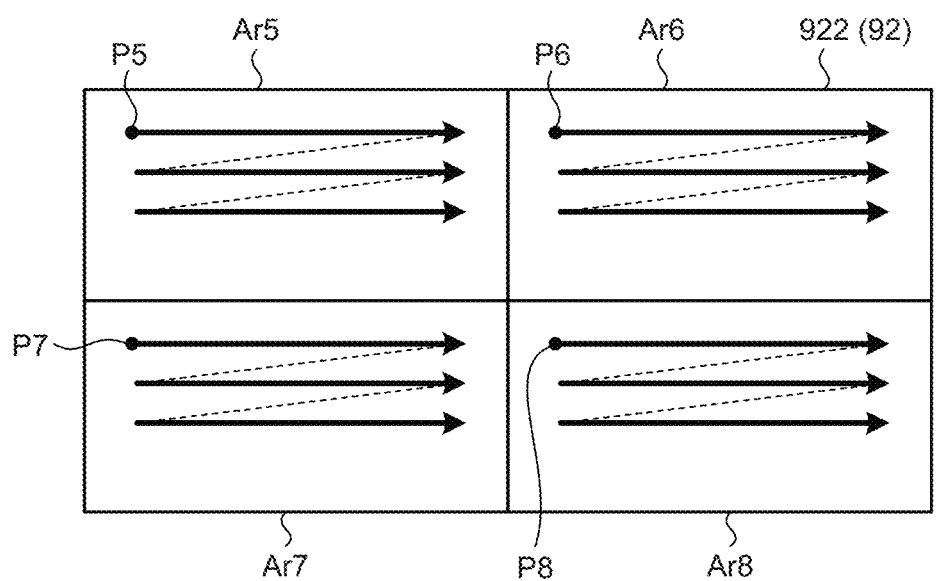
FIG. 7 is a view illustrating the operation of the memory controller in the fluorescence observation mode.

FIGS. 6 and 7 are views illustrating the operation of the memory controller 941 in the fluorescence observation mode. Specifically, FIG. 6 is a view illustrating writing of the left-eye and right-eye normal light images and the left-eye and right-eye fluorescence images to the first memory 92. FIG. 7 is a view illustrating reading of the left-eye and right-eye normal light images and a left-eye and right-eye fluorescence images from the first memory 92. Incidentally, FIGS. 6 and 7 schematically illustrate a specific bank 922 among the plurality of banks in the first memory 92. The bank 922 has the same memory capacity as the bank 921 (in the present embodiment, the memory capacity corresponding to the amount of data of an image having the number of pixels of 4K). In addition, the entire area in the bank 922 is evenly divided into four areas of fifth to eighth divided areas Ar5 to Ar8 in a rice crossed square shape in FIGS. 6 and 7. That is, each of the fifth to eighth divided areas Ar5 to Ar8 has the same memory capacity as each of the first to fourth divided areas Ar1 to Ar4 (in the present embodiment, the memory capacity corresponding to the amount of data of an image having the number of pixels of full HD). Incidentally, the fifth to eighth divided areas Ar5 to Ar8 in the bank 922 correspond to first to fourth memory areas according to the present disclosure, respectively.

Specifically, the memory controller 941 sequentially writes the left-eye normal light images in raster units (the number of pixels: full HD), sequentially output from the left-eye imaging unit 51 and received by the communication unit 91, to the fifth divided area Ar5 in the bank 922 per line as indicated by arrows and broken lines in FIG. 6. In addition, the memory controller 941 sequentially writes the right-eye normal light images in raster units (the number of pixels: full HD), sequentially output from the right-eye imaging unit 52 and received by the communication unit 91, to the sixth divided area Ar6 in the bank 922 per line at the same write timing as the left-eye normal light images.

Further, the memory controller 941 writes each one frame of the left-eye and right-eye normal light images (the number of pixels: full HD) to each of the fifth and sixth divided areas Ar5 and Ar6, and then, sequentially writes the left-eye fluorescence images in raster units (the number of pixels: full HD), sequentially output from the left-eye imaging unit 51 and received by the communication unit 91, to the seventh divided area Ar7 in the bank 922 per line as indicated by arrows and broken lines in FIG. 6. In addition, the memory controller 941 sequentially writes the right-eye fluorescence images in raster units (the number of pixels: full HD), sequentially output from the right-eye imaging unit 52 and received by the communication unit 91, to the eighth divided area Ar8 in the bank 922 per line at the same write timing as the left-eye fluorescence images.

Incidentally, one arrow illustrated in FIG. 6 indicates an image for one line in each of the left-eye and right-eye normal light images (the number of pixels: full HD) and the left-eye and right-eye fluorescence images (the number of pixels: full HD). In addition, in FIGS. 6 and 7, arrows at the same timing (write timing and read timing) in time are arrows having the same thickness. That is, arrows indicating the write timings of the left-eye and right-eye normal light images (the number of pixels: full HD) have the same thickness (thin arrows). On the other hand, arrows indicating the write timings of the left-eye and right-eye fluorescence images (the number of pixels: full HD) have the same thickness, the thickness being different (thick arrow) from the arrows indicating the write timings of the left-eye and right-eye normal light images.

In addition, the memory controller 941 sequentially reads the left-eye and right-eye normal light images (the number of pixels: full HD) and the left-eye and right-eye fluorescence images (the number of pixels: full HD) written in the fifth to eighth divided areas Ar5 to Ar8, respectively, from fifth to eighth storage positions P5 to P8 per line substantially at the same time as the timing of starting to write the left-eye and right-eye fluorescence images (the number of pixels: full HD) from the seventh and eighth storage positions P7 and P8 as indicated by the arrows and dashed lines in FIG. 7. Incidentally, one arrow illustrated in FIG. 7 indicates an image for one line in each of the left-eye and right-eye normal light images (the number of pixels: full HD) and the left-eye and right-eye fluorescence images (the number of pixels: full HD).

Here, pixel data stored at the fifth storage position P5 is pixel data of a pixel at an upper left corner position in the left-eye normal light image (the number of pixels: full HD). In addition, pixel data stored at the sixth storage position P6 is pixel data of a pixel at an upper left corner position in the right-eye normal light image (the number of pixels: full HD). Further, pixel data stored at the seventh storage position P7 is pixel data of a pixel at an upper left corner position in the left-eye fluorescence image (the number of pixels: full HD). In addition, pixel data stored at the eighth storage position P8 is pixel data of a pixel at an upper left corner position in the right-eye fluorescence image (the number of pixels: full HD).

Further, the read left-eye normal light images (the number of pixels: full HD) are sequentially input to the first image processor 942 per line. In addition, the read right-eye normal light images (the number of pixels: full HD) are sequentially input to the second image processor 943 per line. Further, the read left-eye fluorescence images (the number of pixels: full HD) are sequentially input to the third image processor 944 per line. In addition, the read right-eye fluorescence images (the number of pixels: full HD) are sequentially input to the fourth image processor 945 per line.

After Step S12, the first to fourth image processors 942 to 945 execute image processing in parallel on the input left-eye and right-eye normal light images (the number of pixels: full HD) and left-eye and right-eye fluorescence images (the number of pixels: full HD) (Step S13). Here, the first and second image processors 942 and 943 execute the first image processing on the input left-eye and right-eye normal light images (the number of pixels: full HD), respectively. On the other hand, the third and fourth image processors 944 and 945 execute the second image processing on the input left-eye and right-eye fluorescence images (the number of pixels: full HD), respectively.

After Step S13, the superimposed image generation unit 946 generates left-eye and right-eye fluorescence superimposed images SL and SR (see FIG. 8) as illustrated below (Step S14).

Specifically, the superimposed image generation unit 946 superimposes corresponding pixels of the left-eye normal light image (the number of pixels: full HD) on which the first image processing has been executed and the left-eye fluorescence image (the number of pixels: full HD) on which the second image processing has been executed on each other to generate the left-eye fluorescence superimposed image SL (the number of pixels: full HD). In addition, the superimposed image generation unit 946 superimposes corresponding pixels of the right-eye normal light image (the number of pixels: full HD) on which the first image processing has been executed and the right-eye fluorescence image (the number of pixels: full HD) on which the second image processing has been executed on each other to generate the right-eye fluorescence superimposed image SR (the number of pixels: full HD).

Incidentally, examples of the superimposition may include a so-called alpha blending process. The alpha blending process is a process of superimposing pixel values (RGB values) of a first corresponding pixel corresponding to a target pixel to be generated in a superimposed image (left-eye and right-eye fluorescence superimposed images) in a background image (left-eye and right-eye normal light images) and RGB values of a specific pseudo color on each other at a ratio using an alpha value for pixel values (RGB values) of the target pixel. The alpha value is a value based on a fluorescent component of a second corresponding pixel corresponding to the target pixel in a fluorescence image (left-eye and right-eye fluorescence images).

After Step S14, the display control unit 947 generates a display image as illustrated below (Step S15).

Figure 8:
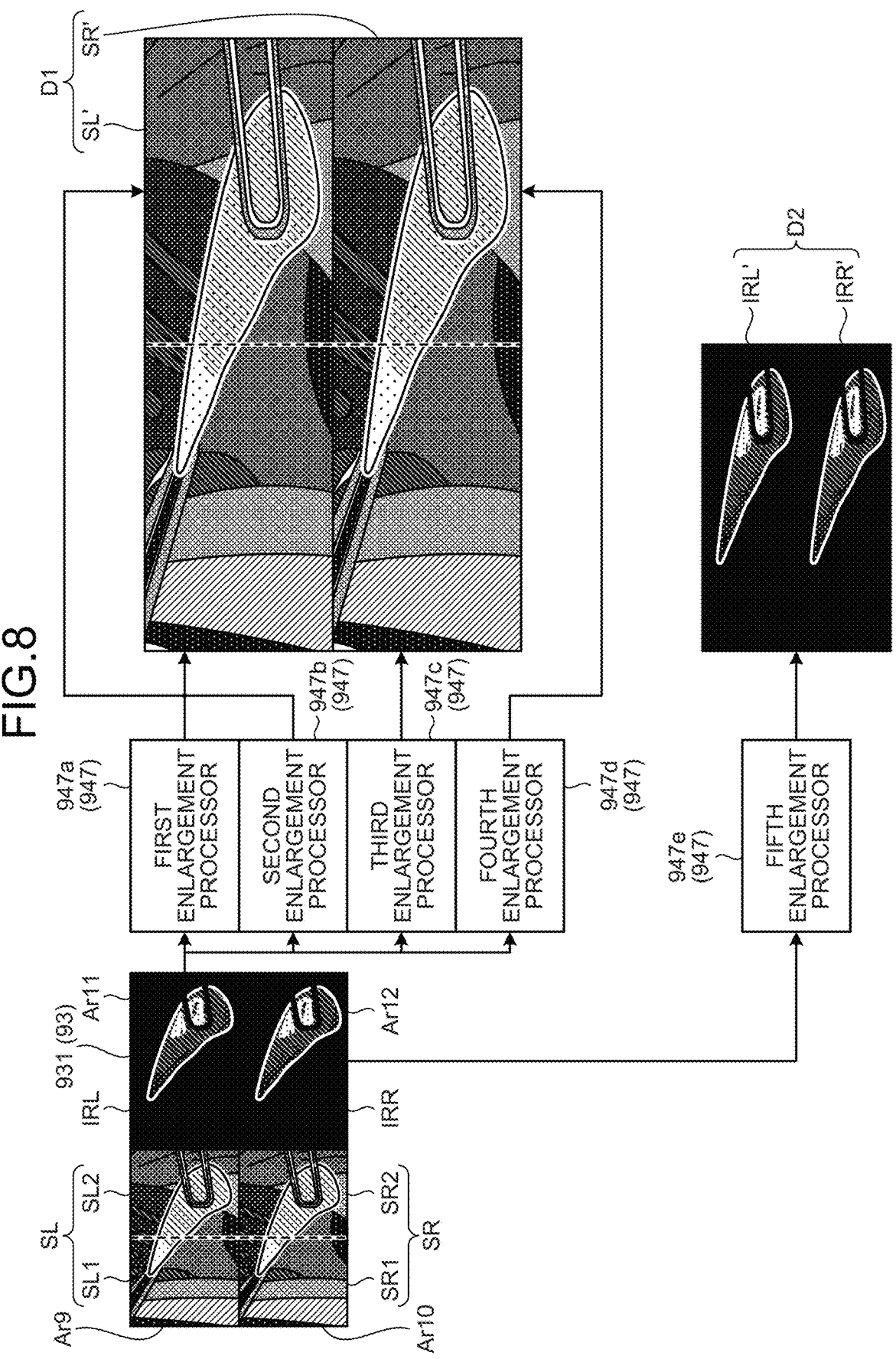
FIG. 8 is a diagram illustrating a function of a display control unit.
Figure 9:
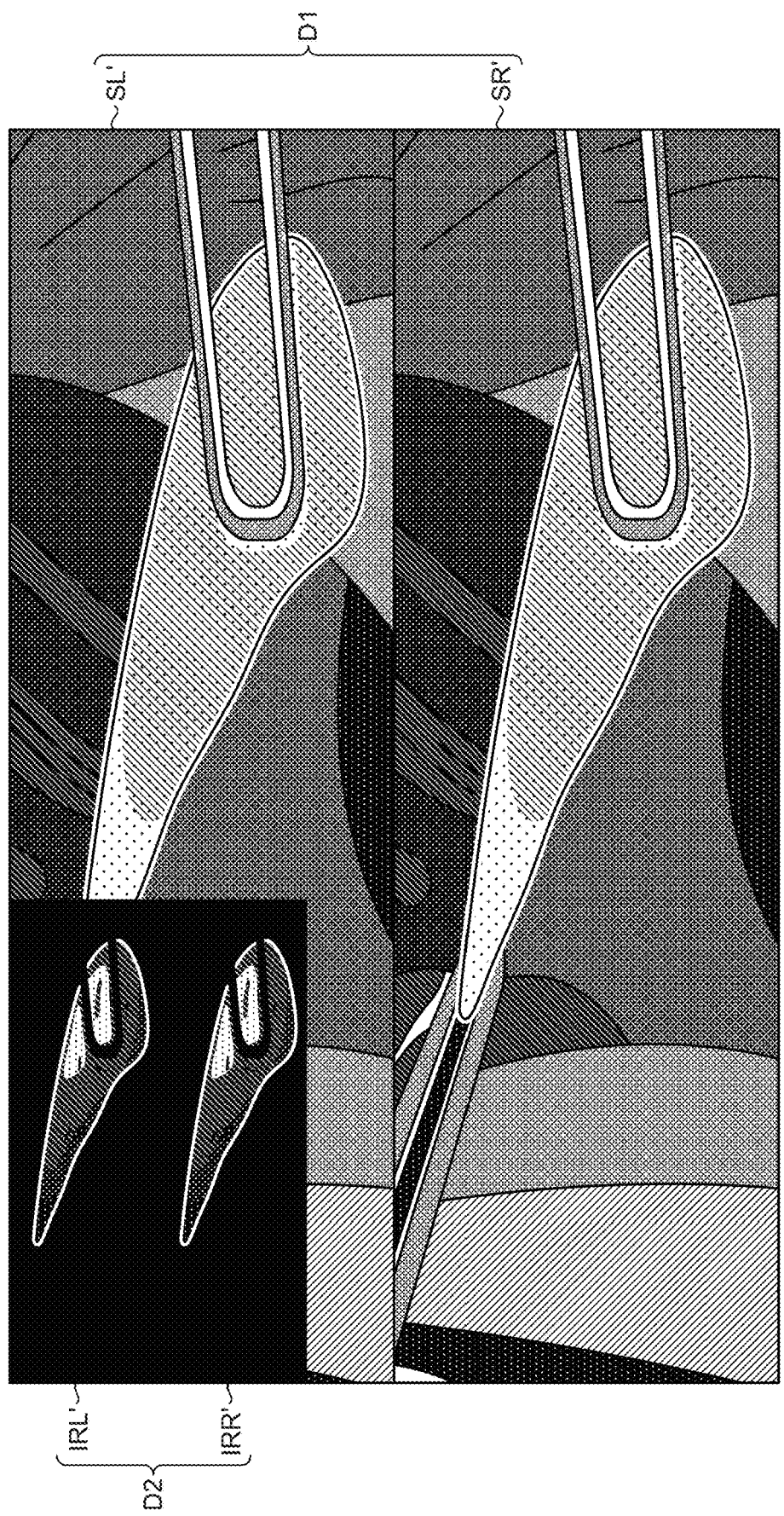
FIG. 9 is a view illustrating the function of the display control unit.

FIGS. 8 and 9 are views illustrating the function of the display control unit 947. Specifically, in FIG. 8, reference signal "931" schematically indicates a specific bank among a plurality of banks in the second memory 93.

In the present embodiment, the bank 931 has a memory capacity corresponding to the amount of data of an image having the number of pixels of 4K. In addition, the entire area in the bank 931 is evenly divided into four areas of ninth to twelfth divided areas Ar9 to Ar12 in a rice crossed square shape in FIG. 8. That is, in the present embodiment, each of the ninth to twelfth divided areas Ar9 to Ar12 has a memory capacity corresponding to the amount of data of an image having the number of pixels of full HD. In addition, in FIG. 8, the reference sign "IRL" indicates a left-eye fluorescence image (the number of pixels: full HD) on which the second image processing has been executed. In addition, in FIG. 8, the reference sign "IRR" indicates a right-eye fluorescence image (the number of pixels: full HD) on which the second image processing has been executed. Incidentally, in the left-eye and right-eye fluorescence images IRL and IRR, an area that looks bright is an area where the intensity of a captured fluorescent component is high. In addition, in FIG. 8, reference signs "947a" to "947e" schematically indicate first to fifth enlargement processors constituting the display control unit 947. Further, in FIG. 8, reference sign "D1" schematically indicates a display image generated by the display control unit 947. In addition, in FIG. 8, reference sign "D2" schematically indicates a display image generated by the display control unit 947. In the present embodiment, the display images D1 and D2 are three-dimensional images that may be observed stereoscopically by a top-and-bottom method. Incidentally, the display image D1 corresponds to a three-dimensional fluorescence superimposed image according to the present disclosure. In addition, the display image D2 corresponds to a second three-dimensional image according to the present disclosure. FIG. 9 is a view illustrating the display images D1 and D2 displayed on the display device 7.

Specifically, the display control unit 947 selects an image to be used to generate the display image from the left-eye and right-eye normal light images (the number of pixels: full HD) on which the first image processing has been executed, the left-eye and right-eye fluorescence images IRL and IRR (the number of pixels: full HD), and the left-eye and right-eye fluorescence superimposed images SL and SR.

In the present embodiment, a display format in which the display image D2 is displayed as a child image in a picture-in-picture with respect to the display image D1 is set as illustrated in FIG. 9. Therefore, the display control unit 947 selects the left-eye and right-eye fluorescence images IRL and IRR and the left-eye and right-eye fluorescence superimposed images SL and SR from the left-eye and right-eye normal light images (the number of pixels: full HD) on which the first image processing has been executed, the left-eye and right-eye fluorescence images IRL and IRR (the number of pixels: full HD), and the left-eye and right-eye fluorescence superimposed images SL and SR. Further, the display control unit 947 sequentially writes the left-eye and right-eye fluorescence superimposed images SL and SR and the left-eye and right-eye fluorescence images IRL and IRR (the number of pixels: full HD) to the ninth to twelfth divided areas Ar9 to Ar12, respectively, of the bank 931 in the second memory 93 per line at the same timing (FIG. 8).

In addition, the first enlargement processor 947a constituting the display control unit 947 performs enlargement to double the number of horizontal pixels without increasing or decreasing the number of vertical pixels while sequentially reading an image SL1 (FIG. 8) in the left half of the left-eye fluorescence superimposed image SL written in the ninth divided area Ar9 from the ninth divided area Ar9 per line. Incidentally, in FIG. 8, the left-eye fluorescence superimposed image SL is virtually divided into the image SL1 in the left half and an image SL2 in the right half by a broken line.

Similarly, the second enlargement processor 947b constituting the display control unit 947 performs enlargement to double the number of horizontal pixels without increasing or decreasing the number of vertical pixels while sequentially reading the image SL2 in the right half of the left-eye fluorescence superimposed image SL from the ninth divided area Ar9 per line at the same read timing as the image SL1.

Further, the images processed by the first and second enlargement processors 947a and 947b are combined to generate a left-eye fluorescence superimposed image SL' obtained by enlarging the left-eye fluorescence superimposed image SL to have the same number of vertical pixels and the doubled number of horizontal pixels.

In addition, the third enlargement processor 947c constituting the display control unit 947 performs enlargement to double the number of horizontal pixels without increasing or decreasing the number of vertical pixels while sequentially reading an image SR1 (FIG. 8) in the left half of the right-eye fluorescence superimposed image SR written in the tenth divided area Ar10 from the tenth divided area Ar10 per line at the same read timing as the images SL1 and SL2. Incidentally, in FIG. 8, the right-eye fluorescence superimposed image SR is virtually divided into the image SR1 in the left half and an image SR2 in the right half by a broken line.

Similarly, the fourth enlargement processor 947d constituting the display control unit 947 performs enlargement to double the number of horizontal pixels without increasing or decreasing the number of vertical pixels while sequentially reading the image SR2 in the right half of the right-eye fluorescence superimposed image SR from the tenth divided area Ar10 per line at the same read timing as the images SL1, SL2, and SR1.

Further, the images processed by the third and fourth enlargement processors 947c and 947d are combined to generate a right-eye fluorescence superimposed image SR' obtained by enlarging the right-eye fluorescence superimposed image SR to have the same number of vertical pixels and the doubled number of horizontal pixels.

That is, the display control unit 947 generates the display image D1 (the number of pixels: 4K) that is obtained by combining the left-eye and right-eye fluorescence superimposed images SL' and SR' and may be observed stereoscopically by the top-and-bottom method. Further, the display control unit 947 outputs a first video signal for display of the display image D1 (the number of pixels: 4K) to the display device 7 via the second transmission cable 8. As a result, the display device 7 displays the display image D1 (the number of pixels: 4K) based on the first video signal as a parent image in the picture-in-picture as illustrated in FIG. 9.

In addition, the fifth enlargement processor 947e constituting the display control unit 947 reduces the number of vertical pixels to half without increasing or decreasing the number of horizontal pixels while sequentially reading the left-eye fluorescence image IRL written in the eleventh divided area Ar11 from the eleventh divided area Ar11 per line at the same read timing as the images SL1, SL2, SR1, and SR2. In addition, after reading one frame of the left-eye fluorescence image IRL, the fifth enlargement processor 947e reduces the number of vertical pixels to half without increasing or decreasing the number of horizontal pixels while sequentially reading the right-eye fluorescence image IRR written in the twelfth divided area Ar12 sequentially from the twelfth divided area Ar12 per line.

Further, by the processing of the fifth enlargement processor 947e, a left-eye fluorescence image IRL', which has the same number of horizontal pixels and the number of vertical pixels reduced by half as compared with the left-eye fluorescence image IRL, and a right-eye fluorescence image IRR', which has the same number of horizontal pixels and the number of vertical pixels reduced by half as compared with the right-eye fluorescence image IRR, are generated.

That is, the display control unit 947 generates the display image D2 (the number of pixels: full HD) that is obtained by combining the left-eye and right-eye fluorescence images IRL' and IRR' and may be observed stereoscopically by the top-and-bottom method. Further, the display control unit 947 outputs a second video signal for display of the display image D2 (the number of pixels: full HD) to the display device 7 via the second transmission cable 8. As a result, as illustrated in FIG. 9, the display device 7 displays the display image D2 (the number of pixels: full HD) based on the second video signal as the child image in the picture-in-picture.

Incidentally, the above-described display format may be changed in setting according to a user operation on the input unit 96 by a user such as a doctor. Examples of the display format that may be set may include the following first to fourth display formats in addition to the above-described display format in which the picture-in-picture is displayed with the display image D1 as the parent image and the display image D2 as the child image.

The first display format is a display format in which a picture-in-picture is displayed with the display image D1 as a parent image and a first three-dimensional image as a child image. The first three-dimensional image is a stereoscopically observable three-dimensional image generated from left-eye and right-eye normal images (the number of pixels: full HD) on which the first image processing has been executed.

The second display format is a display format in which a picture-in-picture is displayed with the display image D1 as a parent image and the display image D2 and the first three-dimensional image as child images.

The third display format is a display format that displays only the display image D1.

The fourth display format is a display format in which a picture-in-picture is displayed with the display image D1 as a parent image and any one of left-eye and right-eye normal light images and left-eye and right-eye fluorescence images as child images.

Incidentally, the above description has been given using the picture-in-picture as the display format, but the display format is not limited to the picture-in-picture. If a format (composite image display format) that displays (combines) a plurality of pieces of different image information on one screen is adopted, the equivalent functions and effects are achieved regardless of the display format of the picture-in-picture.

According to the present embodiment described above, the following effects are achieved.

The control device 9 according to the present embodiment generates the stereoscopically observable display image D1 obtained by combining the left-eye and right-eye fluorescence superimposed images SL' and SR'. Therefore, a doctor or the like may easily excise or suture a lesion while confirming the display image D1 having the sense of depth displayed on the display device 7. Therefore, the convenience may be improved with the control device 9 according to the present embodiment.

In addition, the control device 9 according to the present embodiment generates the stereoscopically observable display image D2 obtained by combining the left-eye and right-eye fluorescence images IRL' and IRR' to use the display image D2 as the child image displayed in the picture-in-picture with respect to the display image D1. Therefore, a doctor or the like may confirm both the display images D1 and D2 displayed on the display device 7, and more easily grasp a position of a lesion and more easily excise or suture the lesion.

In addition, the control device 9 according to the present embodiment executes the image processing in parallel on the first to fourth divided images using the first to fourth image processors 942 to 945 in the normal observation mode. On the other hand, the control device 9 executes the image processing in parallel on the left-eye and right-eye normal light images and the left-eye and right-eye fluorescence images using the first to fourth image processors 942 to 945 in the fluorescence observation mode.

That is, the image processor that executes the image processing in parallel on the first to fourth divided images and the image processor that executes the image processing in parallel on the left-eye and right-eye normal light images and the left-eye and right-eye fluorescence images may be configured as the common image processor. Therefore, it is possible to generate an image suitable for observation without increasing a circuit scale.

OTHER EMBODIMENTS

The modes for carrying out the present disclosure have been described hereinbefore. However, the present disclosure is not limited only to the embodiments described above.

Although the three-dimensional images stereoscopically observable by the top-and-bottom method are illustrated as the display images D1 and D2 in the above-described embodiment, the present disclosure is not limited thereto, and a display image that is a three-dimensional image that may be stereoscopically observed by a side-by-side or line-by-line method may be generated.

In the above-described embodiment, the left-eye and right-eye normal light images used when generating the left-eye and right-eye fluorescence superimposed images may be the following images by the first image processing executed by the first and second image processors 942 and 943.

That is, the first and second image processors 942 and 943 remove r values in the left-eye and right-eye normal light images to leave only g values and b values for conversion into images that do not include R in pixel values. Further, the superimposed image generation unit 946 superimposes corresponding pixels of the converted images and the left-eye and right-eye fluorescence images on each other to generate left-eye and right-eye fluorescence superimposed images.

The number of each of the first to fourth image processors according to the present disclosure is one in the above-described embodiment, but may be two or more without being limited thereto. For example, in a case where a left-eye normal light image or a right-eye normal light image having the number of pixels of 8K is processed in the normal observation mode, it is necessary to provide a total of sixteen image processors in which the number of each of the first to fourth image processors according to the present disclosure is four when assuming the use of the image processor in which the maximum amount of data that may be processed is the amount of data of a full HD image as in the above-described embodiment.

The image sensors 513 and 523 are configured using the image sensor that generates the image having the number of pixels of 4K in the above-described embodiment, but may be configured using an image sensor that generates an image having another number of pixels without being limited thereto.

In the above-described embodiment, a configuration in which only the fluorescence observation mode is provided without providing the normal observation mode may be adopted.

Figure 10:
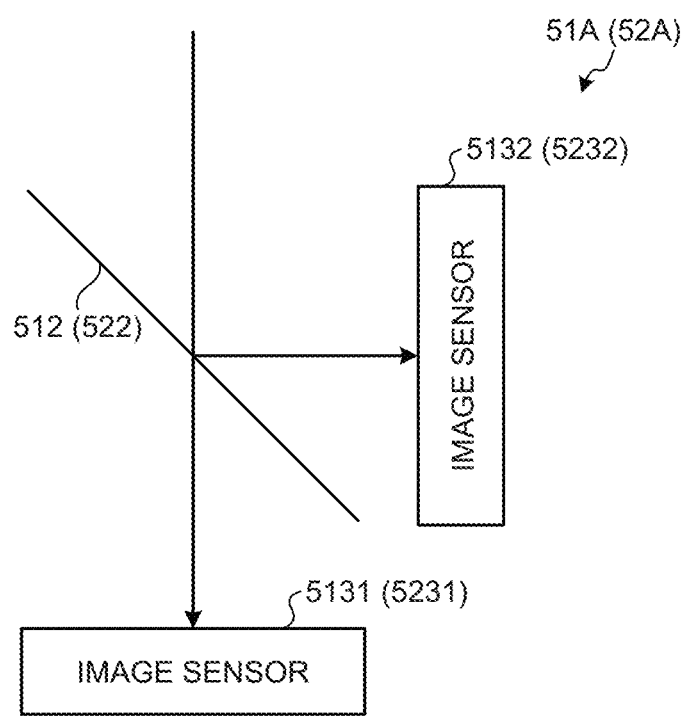
FIG. 10 is a view illustrating a modification of the embodiment.

FIG. 10 is a view illustrating a modification of the embodiment. Incidentally, in the modification illustrated in FIG. 10, the left-eye imaging unit 51 is described as a left-eye imaging unit 51A, and the right-eye imaging unit 52 is described as a right-eye imaging unit 52A for convenience of the description.

Although the light in the first wavelength band and the excitation light in the second wavelength band are emitted in a time-division manner in the fluorescence observation mode in the above-described embodiment, the present disclosure is not limited thereto. For example, on a side where the light in the first wavelength band and the excitation light in the second wavelength band are emitted and captured at the same time, the light in the first wavelength band and the excitation light and fluorescence in the second wavelength band are separated by a filter 512 (522) provided in an optical path of the left-eye imaging unit 51A (right-eye imaging unit 52A) as illustrated in FIG. 10. The filter 512 corresponds to a first filter according to the present disclosure. The filter 522 corresponds to a second filter according to the present disclosure. Further, two image sensors 5131 (5231) and 5132 (5232) are provided in the left-eye imaging unit 51A (right-eye imaging unit 52A). The image sensor 5131 is an image sensor having sensitivity to the light in the first wavelength band, and corresponds to the first image sensor according to the present disclosure. The image sensor 5231 is an image sensor having sensitivity to the light in the first wavelength band, and corresponds to a second image sensor according to the present disclosure. The image sensor 5132 is an image sensor having sensitivity to the light in the second wavelength band, and corresponds to a third image sensor according to the present disclosure. The image sensor 5232 is an image sensor having sensitivity to the light in the second wavelength band, and corresponds to a fourth image sensor according to the present disclosure. That is, a configuration may be adopted in which the two image sensors 5131 (5231) and 5132 (5232) are provided in the left-eye imaging unit 51A (right-eye imaging unit 52A) and these two image sensors 5131 (5231) and 5132 (5232) capture optical images in the first and second wavelength bands, respectively.

Further, as described above, the filter groups of R, G, and B constituting the color filters 513a and 523a of the image sensors 513 and 523 transmit not only the light in the wavelength bands of R, G, and B but also the near-infrared excitation light and fluorescence. Further, the image sensors 513 and 523 have sensitivity not only to the light in the respective wavelength bands of R, G, and B, but also to the light in wavelength bands of the near-infrared excitation light and fluorescence. Utilizing this characteristic, it may be configured such that image information obtained by the image sensors 513 and 523 is separated by the observation image generation unit 94 into optical image information in the first wavelength band and optical image information in the second wavelength band to generate left-eye and right-eye fluorescence superimposed images.

In addition, it may be configured such that a color filter having sensitivity mainly to light in wavelength bands of near-infrared excitation light and fluorescence is added to the color filters 513a and 523a of the imaging image sensors 513 and 523 described above, image information obtained by the image sensors 513 and 523 is separated by the observation image generation unit 94 to acquire optical image information in the first wavelength band and optical image information in the second wavelength band, and left-eye and right-eye fluorescence superimposed images are generated.

Although the light in the first wavelength band is white light and the excitation light in the second wavelength band is near-infrared excitation light in the above-described embodiment, the present disclosure is not limited thereto. As the first and second light sources 31 and 32, other configurations may be adopted as long as the first light source 31 emits light in a first wavelength band and the second light source 32 emits light in a second wavelength band different from the first wavelength band. At this time, the first and second wavelength bands may be partially overlapping bands or may be bands which do not overlap at all.

Meanwhile, there is known photodynamic diagnosis (PDD), which is one of cancer diagnostic methods for detecting cancer cells.

In the photodynamic diagnosis, a photosensitive substance such as 5-aminolevulinic acid (hereinafter referred to as 5-ALA) is used. The 5-ALA is a natural amino acid originally contained in a living body of an animal or a plant. This 5-ALA is taken into a cell after administration into the body and biosynthesized into protoporphyrin in a mitochondrion. Further, the protoporphyrin is excessively accumulated in the cancer cell. In addition, the protoporphyrin excessively accumulated in the cancer cell has photoactivity. Therefore, when excited with excitation light (for example, blue visible light in a wavelength band of 375 nm to 445 nm), the protoporphyrin emits fluorescence (for example, red fluorescence in a wavelength band of 600 nm to 700 nm). The cancer diagnostic method in which a light-sensitive substance is used to cause the cancer cell to emit the fluorescence in this manner is called photodynamic diagnosis.

Further, in the above-described embodiment, the first light source 31 may be configured using an LED that emits white light, and the second light source 32 may be configured using a semiconductor laser that emits excitation light that excites protoporphyrin (for example, blue visible light in the wavelength band of 375 nm to 445 nm). Even in the case of adopting such a configuration, the same effects as those of the above-described embodiment may be obtained.

Although the first and second periods are set to alternately repeat in the fluorescence observation mode in the embodiment described above, the present disclosure is not limited thereto, and may be configured such that at least one of the first and second periods is continuous and a frequency ratio of the first and second periods is a ratio other than 1:1.

Although the medical image processing device according to the present disclosure is mounted on the medical observation system 1 in which the insertion section 2 is configured using the rigid endoscope in the above-described embodiment, the present disclosure is not limited thereto. For example, the medical image processing device according to the present disclosure may be mounted on a medical observation system in which the insertion section 2 is configured using a flexible endoscope. In addition, the medical image processing device according to the present disclosure may be mounted on a medical observation system such as a surgical microscope (see, for example, JP 2016-42981 A) that magnifies and observes a predetermined visual field area in a subject (inside a living body) or on a surface of the subject (living body surface).

In the above-described embodiment, some configurations of the camera head 5 and some configurations of the control device 9 may be provided in the connector CN1 or the connector CN2, for example.

With the medical image processing device and the medical observation system according to the present disclosure, the convenience may be improved.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical image processing device comprising:
    a first captured image acquisition circuit configured to acquire a first left-eye image and a first right-eye image having parallax each of which is obtained by capturing light from an observation target irradiated with light in a first wavelength band, the observation target emitting fluorescence when irradiated with excitation light in a second wavelength band different from the first wavelength band;
    a second captured image acquisition circuit configured to acquire a second left-eye image and a second right-eye image having parallax each of which is obtained by capturing the fluorescence from the observation target irradiated with the excitation light;
    a superimposed image generation circuit configured to superimpose corresponding pixels of the first left-eye image and the second left-eye image on each other to generate a left-eye fluorescence superimposed image and superimpose corresponding pixels of the first right-eye image and the second right-eye image on each other to generate a right-eye fluorescence superimposed image;
    a display control circuit configured to generate a display image from the first left-eye image, the first right-eye image, the second left-eye image, the second right-eye image, the left-eye fluorescence superimposed image, and the right-eye fluorescence superimposed image,
    wherein the display image includes a stereoscopically observable three-dimensional fluorescence superimposed image generated from the left-eye fluorescence superimposed image and the right-eye fluorescence superimposed image;
    a first image processor configured to execute image processing on the first left-eye image;
    a second image processor configured to execute image processing on the first right-eye image;
    a third image processor configured to execute image processing on the second left-eye image;
    a fourth image processor configured to execute image processing on the second right-eye image;
    a mode switching circuit configured to switch between a first observation mode or a second observation mode; and
    a control circuit configured to
    output the first left-eye image, the first right-eye image, the second left-eye image, and the second right-eye image to the first image processor, the second image processor, the third image processor, and the fourth image processor, respectively, in the first observation mode, and
    output four divided images divided from one of the first left-eye image and the first right-eye image to the first image processor, the second image processor, the third image processor, and the fourth image processor, in the second observation mode, and
    the superimposed image generation circuit is configured to generate the left-eye fluorescence superimposed image and the right-eye fluorescence superimposed image in the first observation mode.

2. The medical image processing device according to claim 1, wherein
    each of the first left-eye image and the second left-eye image is generated by a first image sensor, and
    each of the first right-eye image and the second right-eye image is generated a second image sensor.

3. The medical image processing device according to claim 2, wherein each of the first image sensor and the second image sensor includes a filter configured to transmit the light in the second wavelength band.

4. The medical image processing device according to claim 2, further comprising:
    a first filter configured to separate the light in the first wavelength band and the light in the second wavelength band;
    the first image sensor configured to receive the light in the first wavelength band separated by the first filter;
    a third image sensor configured to receive the light in the second wavelength band separated by the first filter;
    a second filter configured to separate the light in the first wavelength band and the light in the second wavelength band;
    the second image sensor configured to receive the light in the first wavelength band separated by the second filter; and
    a fourth image sensor configured to receive the light in the second wavelength band separated by the second filter.

5. The medical image processing device according to claim 1, wherein
    the first left-eye image and the first right-eye image are generated based on the light in the first wavelength band, and
    the second left-eye image and the second right-eye image are generated based on the light in the second wavelength band.

6. The medical image processing device according to claim 1, wherein
    the light in the first wavelength band is light emitted in a first period between the first period and a second period which are alternately repeated, and
    the light in the second wavelength band is light emitted in the second period.

7. The medical image processing device according to claim 1, wherein the display image includes
    the three-dimensional fluorescence superimposed image, and
    an image based on the first left-eye image, the first right-eye image, the second left-eye image, and the second right-eye image, the image displayed as a composite image with respect to the three-dimensional fluorescence superimposed image.

8. The medical image processing device according to claim 7, wherein the composite image includes a child image displayed in a picture-in-picture with respect to the three-dimensional fluorescence superimposed image.

9. The medical image processing device according to claim 7, wherein the composite image is at least one of:
a stereoscopically observable first three-dimensional image generated from the first left-eye image and the first right-eye image; and
a stereoscopically observable second three-dimensional image generated from the second left-eye image and the second right-eye image.

10. The medical image processing device according to claim 1, wherein
the first image processor and the second image processor are configured to
execute first image processing on each of the first left-eye image and the first right-eye image in the first observation mode, and
execute the first image processing on each of the divided images in the second observation mode, and
the third image processor and the fourth image processor are configured to
execute second image processing different from the first image processing on each of the second left-eye image and the second right-eye image in the first observation mode, and
execute the first image processing on each of the divided images in the second observation mode.

11. A medical observation system comprising:
a light source configured to emit light in a first wavelength band and excitation light in a second wavelength band different from the first wavelength band;
an imaging circuit configured to
capture light from an observation target irradiated with the light in the first wavelength band to generate a first left-eye image and the first right-eye image having parallax, the observation target emitting fluorescence when irradiated with excitation light, and
capture the fluorescence from the observation target irradiated with the excitation light to generate a second left-eye image and a second right-eye image having parallax; and
the medical image processing device according to claim 1 configured to process the first left-eye image, the first right-eye image, the second left-eye image, and the second right-eye image.

12. The medical image processing device according to claim 1, further comprising:
a memory configured to temporarily store an image; wherein
the control circuit is further configured to
in the first observation mode, write the first left-eye image, the first right-eye image, the second left-eye image, and the second right-eye image to a first memory area, a second memory area, a third memory area, and a fourth memory area, respectively, and
in the second observation mode, write any one of the first left-eye image and the first right-eye image to a fifth memory area in the memory, reads four divided images obtained by dividing the one image from four divided areas in the fifth memory area in which the four divided images have been written.

13. The medical image processing device according to claim 12, wherein
in the memory,
the one image of which a total number of pixels is a first number of pixels is written to the fifth memory area in the second observation mode, and
the first left-eye image, the first right-eye image, the second left-eye image, and the second right-eye image on which reduction processing has been performed and each of which has a total number of pixels being a second number of pixels, the second number of pixels being equal to or smaller than ¼ of the first number of pixels, are written to the first memory area, the second memory area, the third memory area, and the fourth memory area, respectively, in the first observation mode.

14. A method of processing a medical image, comprising:
acquiring a first left-eye image and a first right-eye image having parallax each of which is obtained by capturing light from an observation target irradiated with light in a first wavelength band, the observation target emitting fluorescence when irradiated with excitation light in a second wavelength band different from the first wavelength band;
acquiring a second left-eye image and a second right-eye image having parallax each of which is obtained by capturing the fluorescence from the observation target irradiated with the excitation light;
superimposing corresponding pixels of the first left-eye image and the second left-eye image on each other to generate a left-eye fluorescence superimposed image and superimpose corresponding pixels of the first right-eye image and the second right-eye image on each other to generate a right-eye fluorescence superimposed image;
generating a display image from the first left-eye image, the first right-eye image, the second left-eye image, the second right-eye image, the left-eye fluorescence superimposed image, and the right-eye fluorescence superimposed image, wherein the display image includes a stereoscopically observable three-dimensional fluorescence superimposed image generated from the left-eye fluorescence superimposed image and the right-eye fluorescence superimposed image;
executing image processing on the first left-eye image in a first image processor;
executing image processing on the first right-eye image in a second image processor;
executing image processing on the second left-eye image in a third image processor;
executing image processing on the second right-eye image in a fourth image processor;
switching between a first observation mode or a second observation mode;
in the first observation mode, outputting the first left-eye image, the first right-eye image, the second left-eye image, and the second right-eye image, to the first, second, third, and fourth image processors, and generating the left-eye fluorescence superimposed image and the right-eye fluorescence superimposed image in the first observation mode; and
in the second observation mode, dividing one of the first left-eye image and the first right-eye image into four divided images and outputting the four divided images to the first image processor, the second image processor, the third image processor, and the fourth image processor.

15. The method according to claim 14, wherein
generating each of the first left-eye image and the second left-eye image uses a first image sensor, and
generating each of the first right-eye image and the second right-eye image uses a second image sensor.

16. The method according to claim 15, further comprising transmitting the light in the second wavelength band to each of the first image sensor and the second image sensor.

17. The method according to claim 14, wherein
generating the first left-eye image and the first right-eye image is based on the light in the first wavelength band, and
generating the second left-eye image and the second right-eye image is based on the light in the second wavelength band.

18. The method according to claim 14, further comprising
emitting the light in the first wavelength band in a first period between the first period and a second period which are alternately repeated, and
emitting the light in the second wavelength band is light emitted in the second period.

19. The method according to claim 14, further comprising:
executing first image processing on each of the first left-eye image and the first right-eye image in the first observation mode using the first and second image processors, respectively,
executing the first image processing on each of the divided images in the second Observation mode, using the first and second image processors, respectively,
executing second image processing different from the first image processing on each of the second left-eye image and the second right-eye image in the first observation mode, using the third and fourth image processors, respectively, and
executing the first image processing on each of the divided images in the second Observation mode, using the third and fourth image processors, respectively.

20. The method according to claim 14, further comprising:
temporarily storing an image; and
in the first observation mode, writing the first left-eye image, the first right-eye image, the second left-eye image, and the second right-eye image to a first memory area, a second memory area, a third memory area, and a fourth memory area, respectively, and
in the second observation mode, writing any one of the first left-eye image and the first right-eye image to a fifth memory area in the memory, reads four divided images obtained by dividing the one image from four divided areas in the fifth memory area in which the four divided images have been written.

* * * * *